United States Patent [19]

Holtkamp

[11] Patent Number: Plant 5,604

[45] Date of Patent: Dec. 17, 1985

[54] AFRICAN VIOLET PLANT NAMED BETTY

[75] Inventor: Reinhold Holtkamp, Isselburg, Fed. Rep. of Germany

[73] Assignee: Gessellschaftsvertrag uber die Ergindergemeinschaft "OPTI-MARA", Rees Haffen, Fed. Rep. of Germany

[21] Appl. No.: 568,444

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet plant named Betty characterized by its compact growth habit, dark green serrated leaves, strong, upright flower stems, each of which carries 5–7 and more flowers, the flowers being frilled and waved and mainly white in color with dark purple centers, uniform growth habit, long lasting and non-dropping flowers, and its ability to produce a saleable plant with a fully developed flower head 8–10 weeks after potting.

1 Drawing Figure

The present invention comprises a new and distinct cultivar of African violet plant, botanically known as *Saintpaulia ionantha,* and named Betty.

The new cultivar was referred to during the breeding and selection process by the designation G 12/XV, and is a product of a planned breeding program.

The new cultivar was originated from a cross made in a controlled breeding program in Isselburg, West Germany. The female, or seed parent was a cultivar designated XIX 4158 Red. The male, or pollen parent was a cultivar designated 67 Red Girl.

The new cultivar Betty was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Betty has not been observed under all possible environmental conditions. The phenotype may vary significantly with variations in environment such as temperature, light intensity and day length. The following observations, measurements and values describe the new cultivar as grown in Isselburg, West Germany, and Nashville, Tenn. under greenhouse conditions which closely approximate those generally used in commercial practice.

The following traits have been repeatedly observed and are determined to be basic characteristics of Betty, which in combination distinguish this African violet as a new and distinct cultivar:

1. Compact growth habit.
2. Dark green serrated leaves.
3. Seven to nine strong, upright and wire-like flower stems each carrying 5–7 or more flowers.
4. The flowers are frilled and wavy, with the flower color being mainly white but dark purple in the center; the purple tinging occasionally extends from the center toward the edge of the petals.
5. Uniform growth habit, with the leaf petioles not stretching.

6. Highly floriferous, compact flower head, with the flowers being long lasting and non-dropping.
7. Fast producer, with a saleable pot having a compact flower head being fully developed 8–10 weeks after potting.

The accompanying photograhic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at 3 P.M. in late November in Nashville, Tenn.

Botanical classification: *Saintpaulia ionantha,* Ramat. cv. BETTY.

Parentage:

*Male parent.*—67 Red Girl.

*Female parent.*—XIX 4158 Red.

Propagation: The new cultivar holds its distinguishing characteristics through successive propagations by leaf cuttings and by division of shoots.

Plant: From 5 cm. to 8 cm. tall when grown in pots, and approximately 20–22 cm. in diameter when fully grown.

*Leaves.*—General Form: Oval. Diameter: 50–60 mm. Texture: Leather-like. Aspect: Heavily serrated indentations; shiny. Veins: Pronounced light green; shiny. Color (upperside): Yellow green 147 between A-B. Color (underside): Yellow green 148D. Petiole: Brownish Purple.

*Flowers.*—Buds: Ball-shape. Sepals: Color: Light green. Calyx: Flat funnel. Aspect: Spear shape; hairy. Peduncle: Short and upright.

*Individual flowers.*—Size: 40–45 mm. Color: Upperside: White, with center purple violet 82A. Underside: White, slightly purple. Borne: On upright, short wire-like peduncles. Shape: Violet shape, frilled, wavy. Flowering time: In 8–10 weeks after potting, a saleable plant is produced with a fully developed flower head just above the leaves.

*Reproductive organs.*—Anthers: 2 composed out of 4 cells. Filaments: Bright green ovary. Styles: Light purple; white stigma.

Roots: White when young and active; brownish when older.

Disease resistance: Good as experienced to date.

I claim:

1. A new and distinct cultivar of African violet plant named Betty, as described and illustrated, and particularly characterized by its compact growth habit, dark green serrated leaves, strong, upright flower stems, each of which carries 5–7 and more flowers, the flowers being frilled and waved and mainly white in color with dark purple centers, uniform growth habit, long lasting and non-dropping flowers, and its ability to produce a saleable plant with a fully developed flower head 8–10 weeks after potting.

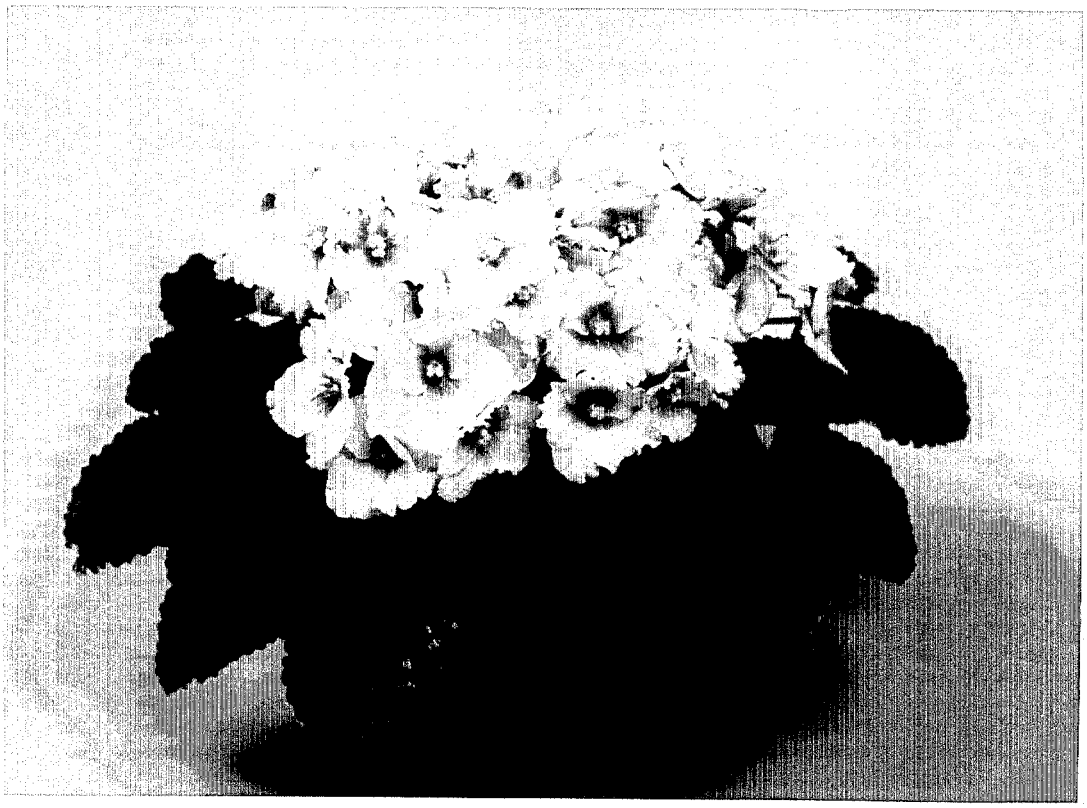

* * * * *